US010285362B2

(12) United States Patent
Warfield et al.

(10) Patent No.: US 10,285,362 B2
(45) Date of Patent: May 14, 2019

(54) **DOWNY MILDEW RESISTANT *IMPATIENS***

(71) Applicant: Ball Horticultural Company, West Chicago, IL (US)

(72) Inventors: Colleen Y. Warfield, Batavia, IL (US); Cornelis van Petersen, Hilversum (NL); Rudolfus A. Brinkkemper, Enkhuizen (NL); Simone E. Crain, Montgomery, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/917,176

(22) Filed: Mar. 9, 2018

(65) Prior Publication Data

US 2018/0271045 A1    Sep. 27, 2018

Related U.S. Application Data

(60) Provisional application No. 62/613,354, filed on Jan. 3, 2018, provisional application No. 62/470,719, filed on Mar. 13, 2017.

(51) Int. Cl.
    *A01H 6/16*      (2018.01)
    *A01H 5/02*      (2018.01)
    *A01H 1/04*      (2006.01)

(52) U.S. Cl.
    CPC ............. *A01H 6/165* (2018.05); *A01H 1/04* (2013.01); *A01H 5/02* (2013.01)

(58) Field of Classification Search
    CPC ...................................... A01H 6/165
    See application file for complete search history.

(56) References Cited

U.S. PATENT DOCUMENTS

| 8,461,416 B2 | 6/2013 | Niblett |
| 2003/0221222 A1 | 11/2003 | Laten |
| 2007/0016976 A1 | 1/2007 | Katagiri et al. |
| 2009/0178162 A1 | 7/2009 | Cooper |

OTHER PUBLICATIONS

Bhattarai et al, International Journal of Molecular Science, vol. 19, 17 pages, published Jul. 15, 2018 (Year: 2018).*
Hansen et al, Virginia Cooperative Extension publication PPWS-19NP "Impatiens Downy Mildew" (Year: 2013).*
International Search Report and Written Opinion regarding International Application No. PCT/US2018/021767, dated Jul. 6, 2018.
Ashrafi et al., "De novo assembly of the pepper transcriptome (*Capsicum annuum*): a benchmark for in silico discovery of SNPs, SSRs and candidate genes," *BMC Genomics* 13:571, 2012.
Bolger et al., "The genome of the stress-tolerant wild tomato species *Solanum pennellii*," *Nature Genetics* 46(9):1034-1039, 2014.
Velasco et al., "A High Quality Draft Consensus Sequence of the Genome of a Heterozygous Grapevine Variety," *Plos One* 12:e1326; 2007.
Venturini et al., "De novo transcriptome characterization of *Vitis vinifera* cv. Corvina unveils varietal diversity," *BMC Genomics* 14:41, 2013.
U.S. Appl. No. 16/129,289, filed Sep. 12, 2018, Warfield et al.

* cited by examiner

*Primary Examiner* — David H Kruse
(74) *Attorney, Agent, or Firm* — Dentons US LLP

(57) ABSTRACT

The present disclosure provides seed and plants of downy mildew resistant *Impatiens* plants. The present disclosure thus relates to the plants, seeds, and tissue cultures of downy mildew resistant *Impatiens* plants, and to methods for producing a downy mildew resistant plant of the present disclosure by crossing such plants with themselves or with another *Impatiens* plant, such as a plant of another genotype, variety, or cultivar. The present disclosure further relates to seeds and plants produced by such crossing. The present disclosure further relates to parts of such plants.

18 Claims, 11 Drawing Sheets

Specification includes a Sequence Listing.

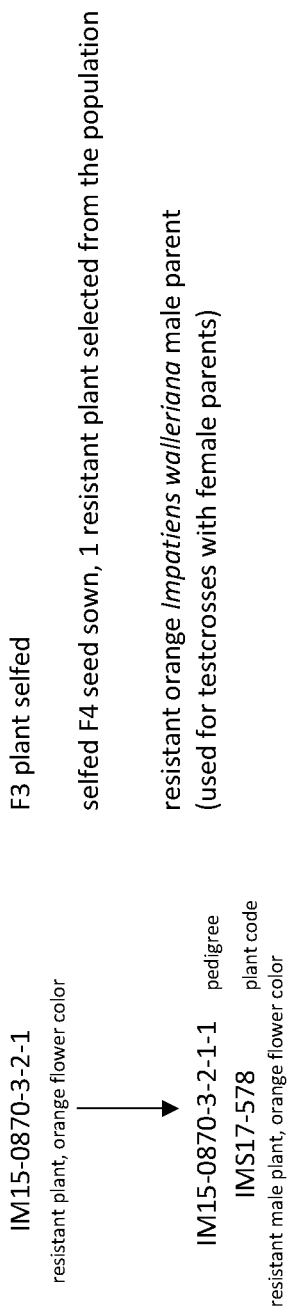
FIG. 3 (Con't)

SEQUENCE LISTING

<160> NUMBER OF SEQ ID NOS: 9

<210> SEQ ID NO 1
<211> LENGTH: 114
<212> TYPE: DNA
<213> ORGANISM: Impatiens sp.

<400> SEQUENCE: 1
ccaacctttc actcagccgt ctgtttccat atcctcatgy ggcttcgatg aactatccat     60
cggtagctca aaatgctccg ctattaccct cttyggtttt aggcwgctaa caga          114

```
<210> SEQ ID NO 2
<211> LENGTH: 114
<212> TYPE: DNA
<213> ORGANISM: Impatiens sp.

<400> SEQUENCE: 2
aacgacgcgt ggccgaagcc ctcgagcgag cgcgaacata ccaagtccty agagcgaacg      60
aggccgagtt cgaagtgata tctcacgagg gaacccacgt cgtggatatm cgta          114

<210> SEQ ID NO 3
<211> LENGTH: 114
<212> TYPE: DNA
<213> ORGANISM: Impatiens sp.

<400> SEQUENCE: 3
acaatggttt gactgtcgta gtyggtggag gagcygcaat tgcagcccat ggatcatcgc      60
tatccamwga agggggatg cttttttggga tcaatggtct tgatgttgat ttcg          114

<210> SEQ ID NO 4
<211> LENGTH: 114
<212> TYPE: DNA
<213> ORGANISM: Impatiens sp.

<400> SEQUENCE: 4
tgaccaatac atcacttgaa aatgttatgt tagtggaaga tatgttcatg aaatcttcta     60
aagagagtkt agtttcttgg aacgtgatga tttctgtcta cttgaagaat tccc          114

<210> SEQ ID NO 5
<211> LENGTH: 114
<212> TYPE: DNA
<213> ORGANISM: Impatiens sp.

<400> SEQUENCE: 5
tgtggtattt ggagatgctc ttagtggttg taaggcgggw gcaggttgtc cttacgctgt     60
tacttacgga gatgggagct cgacttctgg acattttgtg aaggatatcg taca          114

<210> SEQ ID NO 6
<211> LENGTH: 114
<212> TYPE: DNA
<213> ORGANISM: Impatiens sp.

<400> SEQUENCE: 6
ttcaagctgc cattctgtgt ggggagggaa atccacaagt gcgagacctt gtgcttctcg     60
atgtcacwcc tctgtctctt ggarttkatr tacttggagg cattatgtca gtgt          114

<210> SEQ ID NO 7
<211> LENGTH: 114
<212> TYPE: DNA
<213> ORGANISM: Impatiens sp.

<400> SEQUENCE: 7
acagttatag cttagggtag aaacttcggg agagacggag agatgggggc caaactcaca     60
agcaatggas gaagcattgg aagggaggag agaagatggg ttattgggag atgg          114

<210> SEQ ID NO 8
<211> LENGTH: 114
<212> TYPE: DNA
<213> ORGANISM: Impatiens sp.

<400> SEQUENCE: 8
```

```
ttcgaycatc ctctgttgca aaagagcaat cgcgccgatg catccgtaaa caggatcgcy      60
gagcctgacc tcagcctgga atacgagaga gttgacggcg tctrygcggc gatc           114

<210> SEQ ID NO 9
<211> LENGTH: 114
<212> TYPE: DNA
<213> ORGANISM: Impatiens sp.

<400> SEQUENCE: 9
kttcagggac agacgatttt gggccgtgcc ctctattcag aagcgaaccg catacagatt      60
ggagttgacg tcgaagaggg ggrtcttgga taagtgtgac ttcttccggt gaag           114
```

DOWNY MILDEW RESISTANT *IMPATIENS*

REFERENCE TO RELATED APPLICATIONS

This application claims the benefit of U.S. Provisional Application 62/470,719, filed Mar. 13, 2017, and U.S. Provisional Application 62/613,354, filed Jan. 3, 2018, both of which are incorporated herein by reference in their entirety.

INCORPORATION OF SEQUENCE LISTING

The sequence listing that is contained in the file named "BALL037US_ST25.txt," which is 3 kilobytes as measured in Microsoft Windows operating system and was created on Mar. 7, 2018, is filed electronically herewith and incorporated herein by reference.

FIELD OF THE INVENTION

The present disclosure relates to the field of plant breeding and, more specifically, to the development of downy mildew resistant *Impatiens* plants and seeds and hybrids thereof.

BACKGROUND OF THE INVENTION

*Impatiens* downy mildew, caused by *Plasmopara obducens*, is a destructive foliar disease of *Impatiens walleriana* that is capable of causing complete defoliation or plant collapse, especially in landscape plantings under moist conditions and cool nights.

Regional outbreaks of this disease were seen for the first time in landscape beds and container plantings in North America in summer 2011. By the end of the 2012 season, *impatiens* downy mildew had been confirmed in 34 states. However, the occurrence and timing of when the disease was observed within a geographic region was highly variable. In 2013, the distribution of the disease was widespread and similar in distribution to the previous two years, with the addition of infected landscape beds in regions of Colorado, Kansas, Utah and Hawaii. In most regions of the country the occurrence of the disease in 2013 and 2014 was late in the season, similar to what was observed in 2011. Each year since, the disease has been observed in landscapes across the United States and lower Canada. The occurrence is earlier in the southern states (November-February) and later in the northeast and upper midwest (August-October).

Hosts include all cultivars of *Impatiens walleriana*, the common garden *impatiens*, and interspecific hybrids with an *I. walleriana* parent are susceptible. A few wild species of *impatiens* are also susceptible; however, there are no other bedding plant species that are known hosts. Both vegetative propagated and seed-raised *I. walleriana* are susceptible but there is no evidence of seedborne transmission of *P. obducens*. New Guinea *impatiens*, *Impatiens hawkeri*, including Divine, Celebration, Celebrette, and Sunpatiens series have high resistance to this disease.

Sporangia, sac-like structures filled with zoospores, produced on the underside of infected leaves are easily dislodged and can be spread short distances by water splash, and longer distances by air currents. Infected plants not yet showing symptoms may result in the inadvertent movement of the pathogen into greenhouse production facilities or the landscape.

Young plants and immature plant tissues are especially susceptible to infection. Symptoms are often first observed on terminal growth. Seedling cotyledons are highly susceptible to infection. Early symptoms include light-green yellowing or stippling of leaves, downward curling of infected leaves, and white downy-like fungal growth on the undersides of leaves. Advanced symptoms include stunting in both plant height and leaf size when infected at an early stage of development, leaf and flower drop resulting in bare, leafless stems, and infected stems become soft and plants collapse under continued wet and cool conditions as found in landscape plantings. (Warfield C., *Impatiens* Downy Mildew; Guidelines for Growers, 2014; Warfield, C. Downy Mildew of *Impatiens*, GrowerTalks, 2011).

SUMMARY OF THE INVENTION

The present disclosure provides an *Impatiens* plant, for example an *Impatiens walleriana* plant, having resistance to downy mildew relative to a wild type plant, wherein said *Impatiens* plant comprises the genetic source for downy mildew resistance (DMR) found in *Impatiens* sp. T041. A representative sample of seed comprising the genetic source of resistance from *Impatiens* sp. 7511 has been deposited under ATCC Accession No. PTA-123803. The deposited *Impatiens* sp. 7511 seed has the downy mildew resistance trait from *Impatiens* sp. T041. In certain embodiments the *Impatiens* plant having downy mildew resistance comprises a transgene. In other embodiments the plant is inbred, while in yet other embodiments the plant is hybrid. In further embodiments, the plant is a cultivated ornamental variety of *Impatiens*. The present disclosure further provides a plurality of *Impatiens* plants having resistance to downy mildew grown in a field.

The present disclosure also provides a plant part of an *Impatiens* plant having resistance to downy mildew, wherein the plant part comprises at least one cell of said plant. In certain embodiments the plant part is a leaf, pollen, a meristem, a cell, a seed, or an ovule. The present disclosure additionally provides a seed that produces an *Impatiens* plant having resistance to downy mildew.

The present disclosure further provides a method of producing a downy mildew resistant *Impatiens* seed, the method comprising crossing a downy mildew resistant *Impatiens* plant with itself or a second *Impatiens* plant. In some embodiments the method comprises crossing the downy mildew resistant *Impatiens* plant with a second, distinct *Impatiens* plant to produce an F1 hybrid *Impatiens* seed. Thus, the present disclosure also provides an F1 hybrid *Impatiens* seed produced by this method. In particular embodiments, the method further comprises crossing a plant grown from the F1 hybrid *Impatiens* seed with itself or a different *Impatiens* plant to produce a seed of a progeny plant of a subsequent generation, growing a progeny plant of a subsequent generation from the seed of a progeny plant of a subsequent generation and crossing the progeny plant of a subsequent generation with itself or a second plant to produce a progeny plant of a further subsequent generation, and repeating steps (a) and (b) using the progeny plant of a further subsequent generation from step (b) in place of the plant grown from said F1 hybrid *Impatiens* seed in step (a), wherein steps (a) and (b) are repeated with sufficient inbreeding to produce an inbred *Impatiens* plant.

BRIEF DESCRIPTION OF THE DRAWINGS

The following drawings form part of the present specification and are included to further demonstrate certain aspects of the present disclosure. The present disclosure may

DETAILED DESCRIPTION OF THE INVENTION

A. Breeding *Impatiens* Plants

Figure 1:
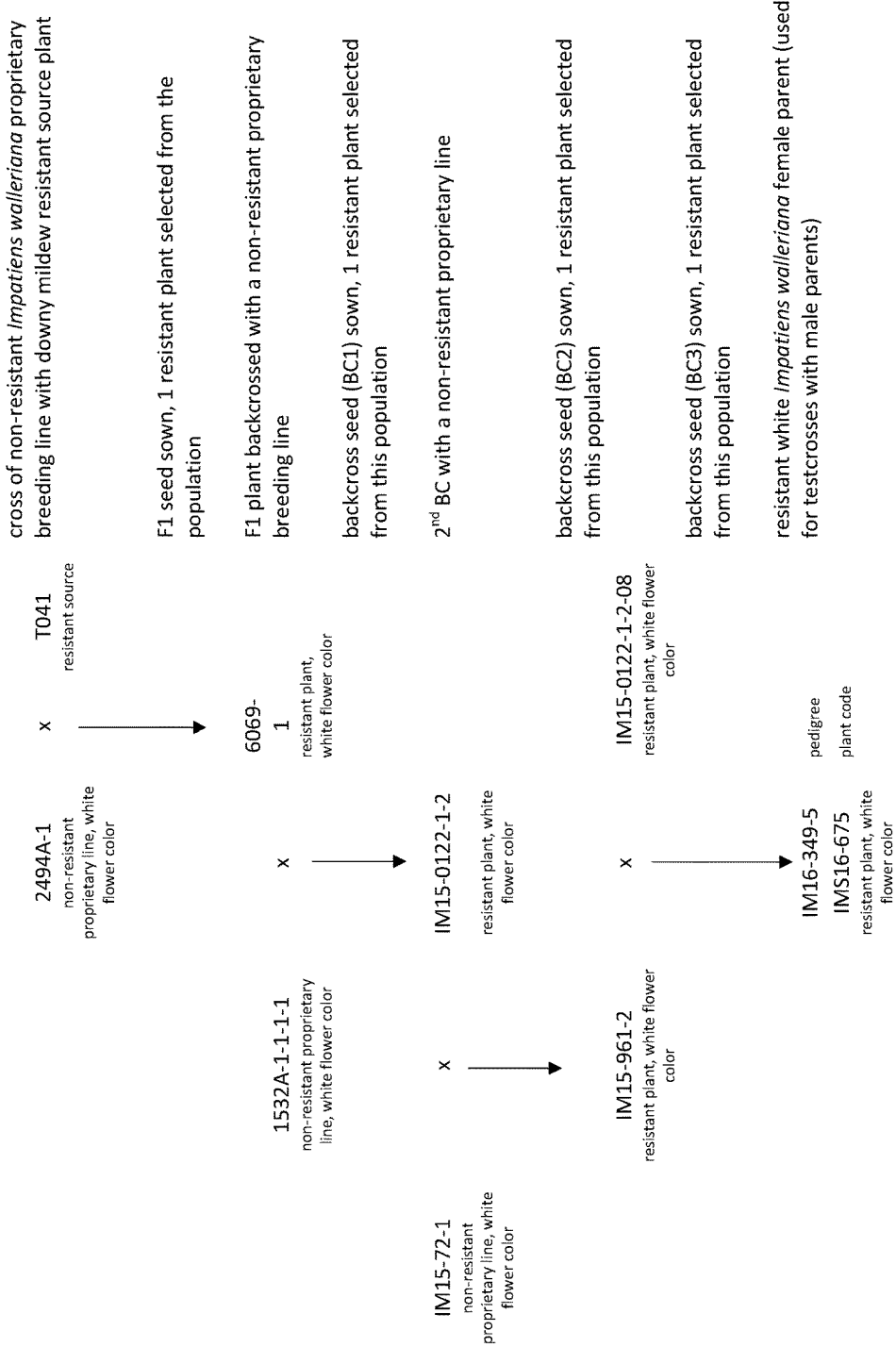
FIG. 1 shows a pedigree chart for IMS16-675 DMR *Impatiens* plant.
Figure 2:
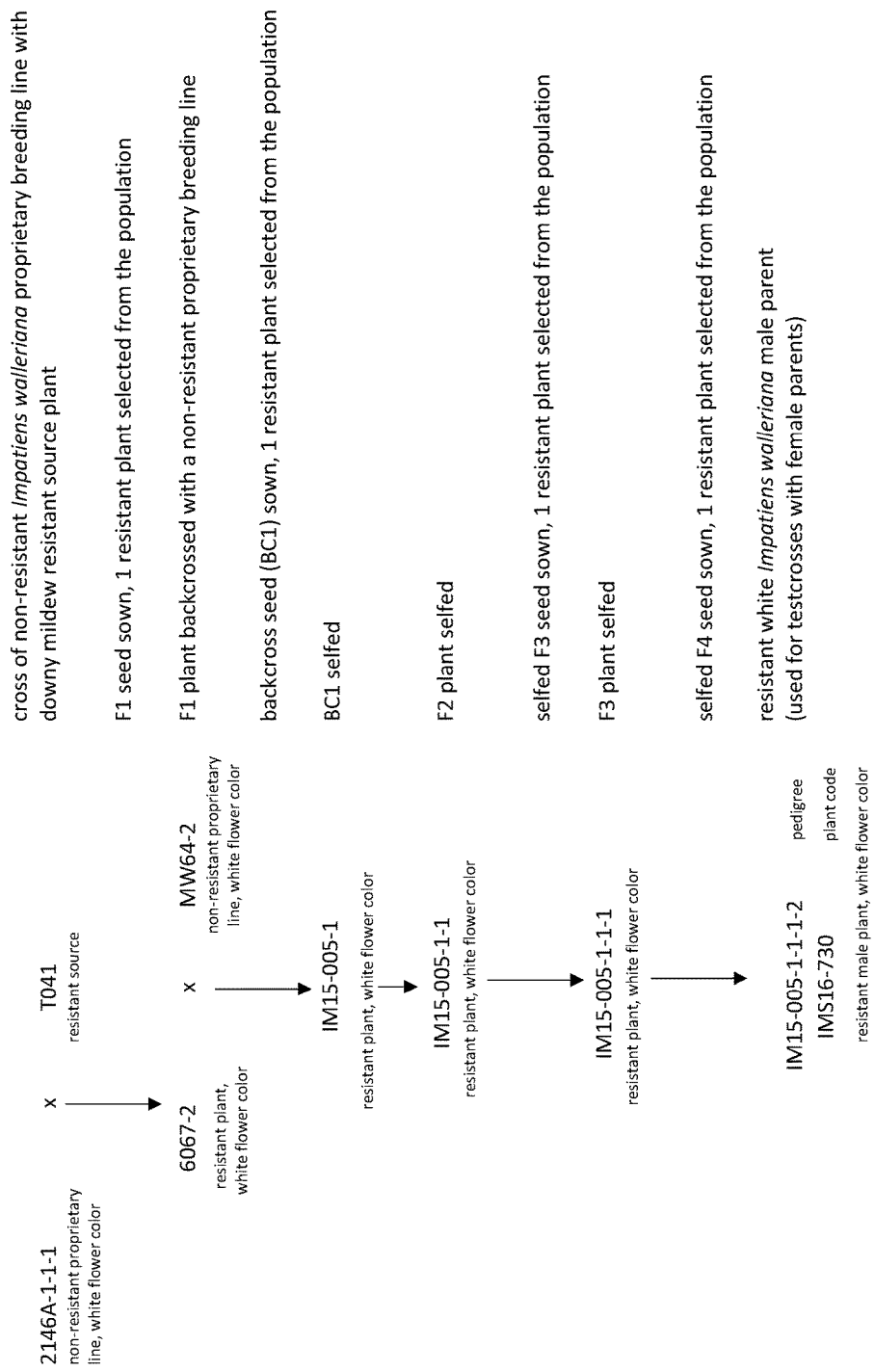
FIG. 2 shows a pedigree chart for IMS16-730 DMR *Impatiens* plant.
Figure 3:
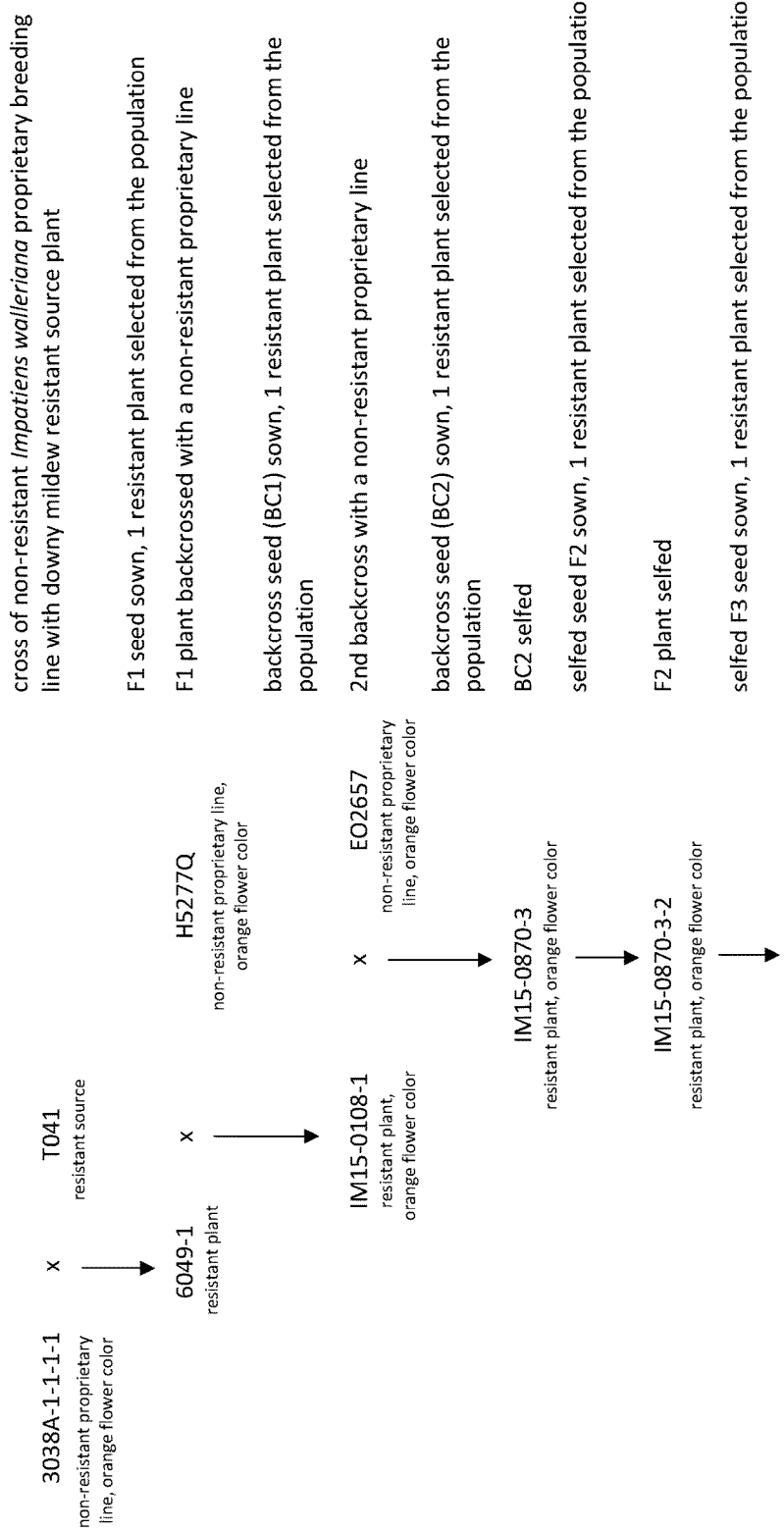
FIG. 3 shows a pedigree chart for IMS17-578 DMR *Impatiens* plant.
Figure 4:
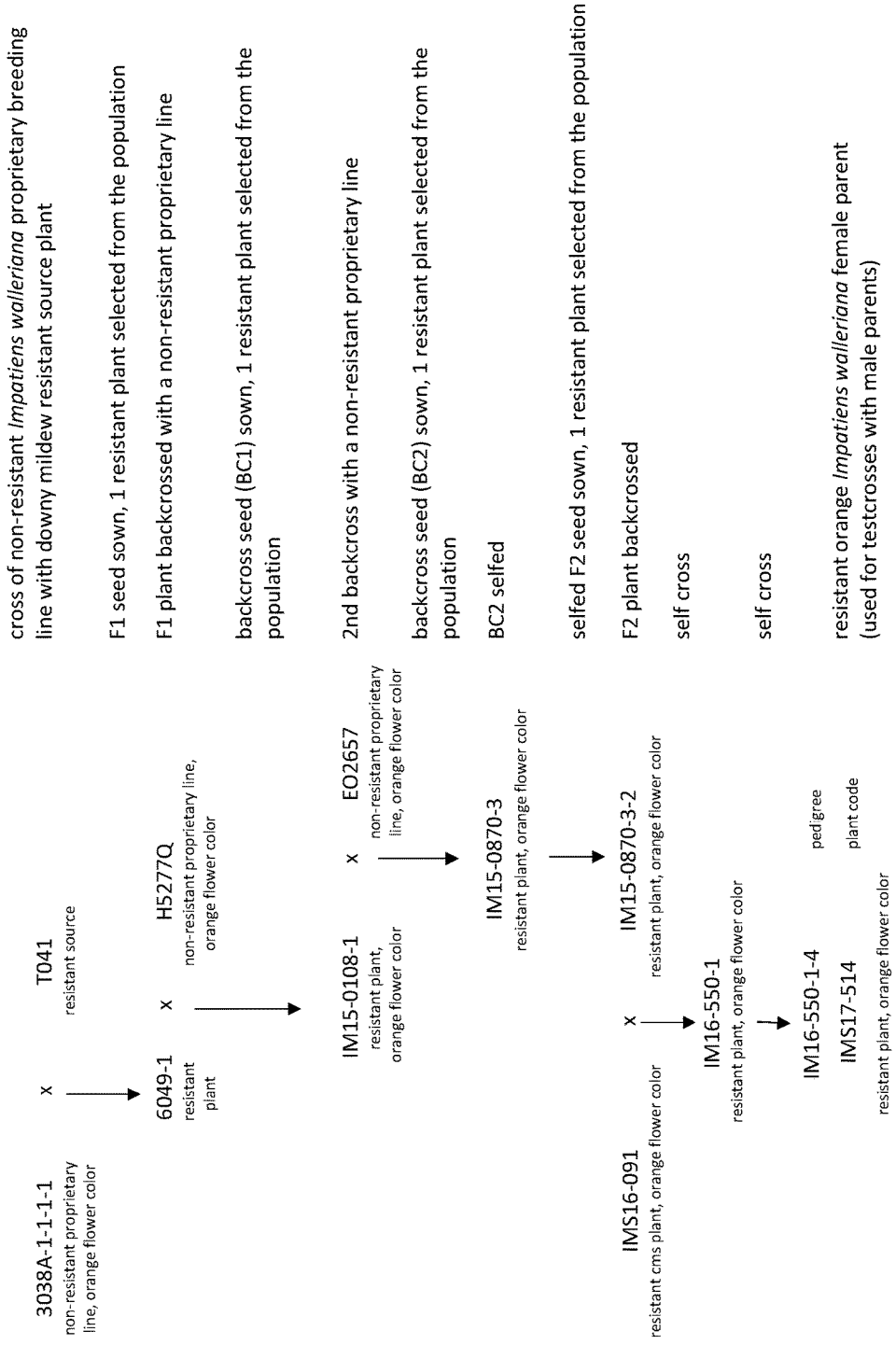
FIG. 4 shows a pedigree chart for IMS17-514 DMR *Impatiens* plant.
Figure 5:
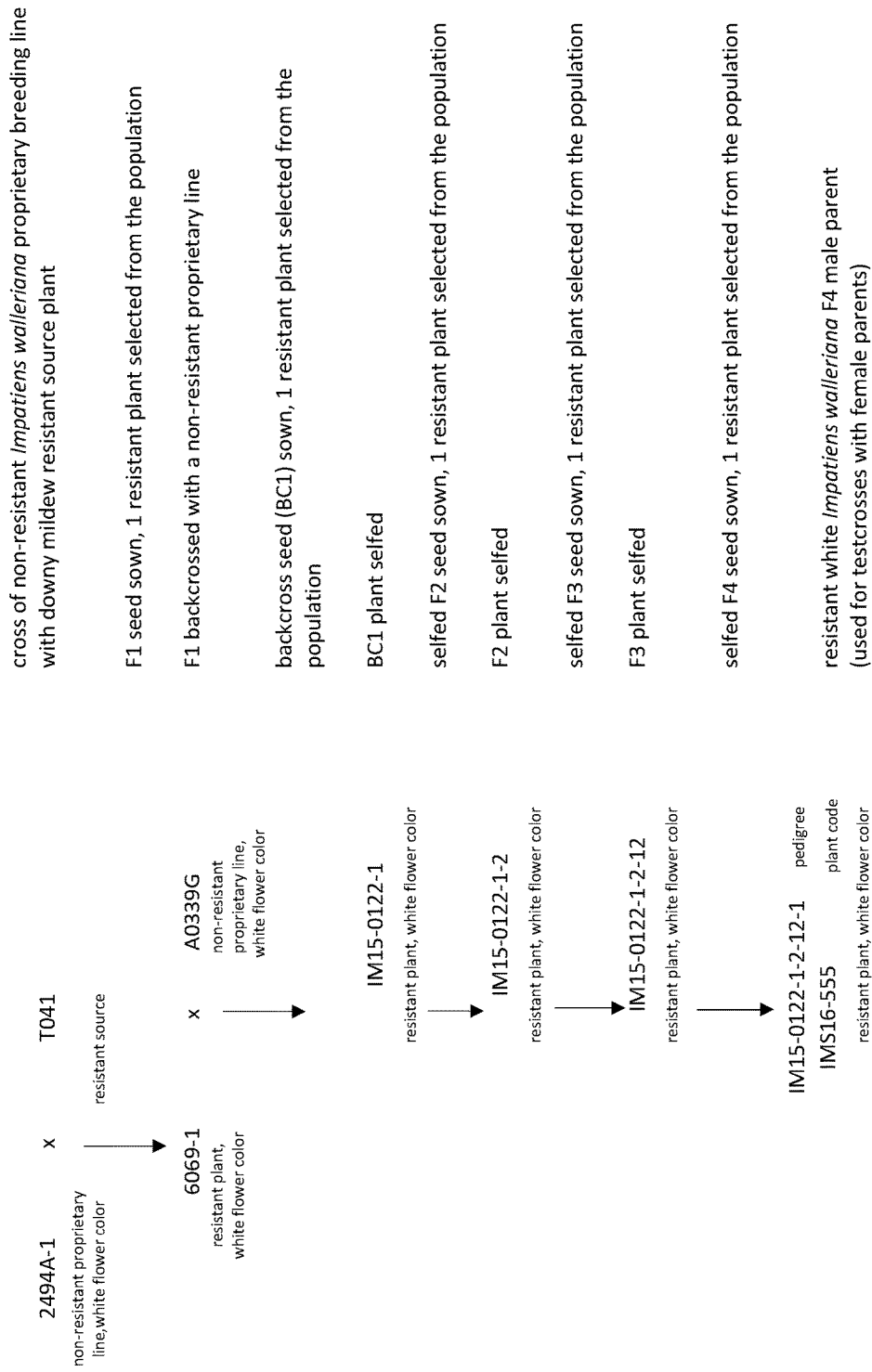
FIG. 5 shows a pedigree chart for IMS16-555 DMR *Impatiens* plant.
Figure 6:
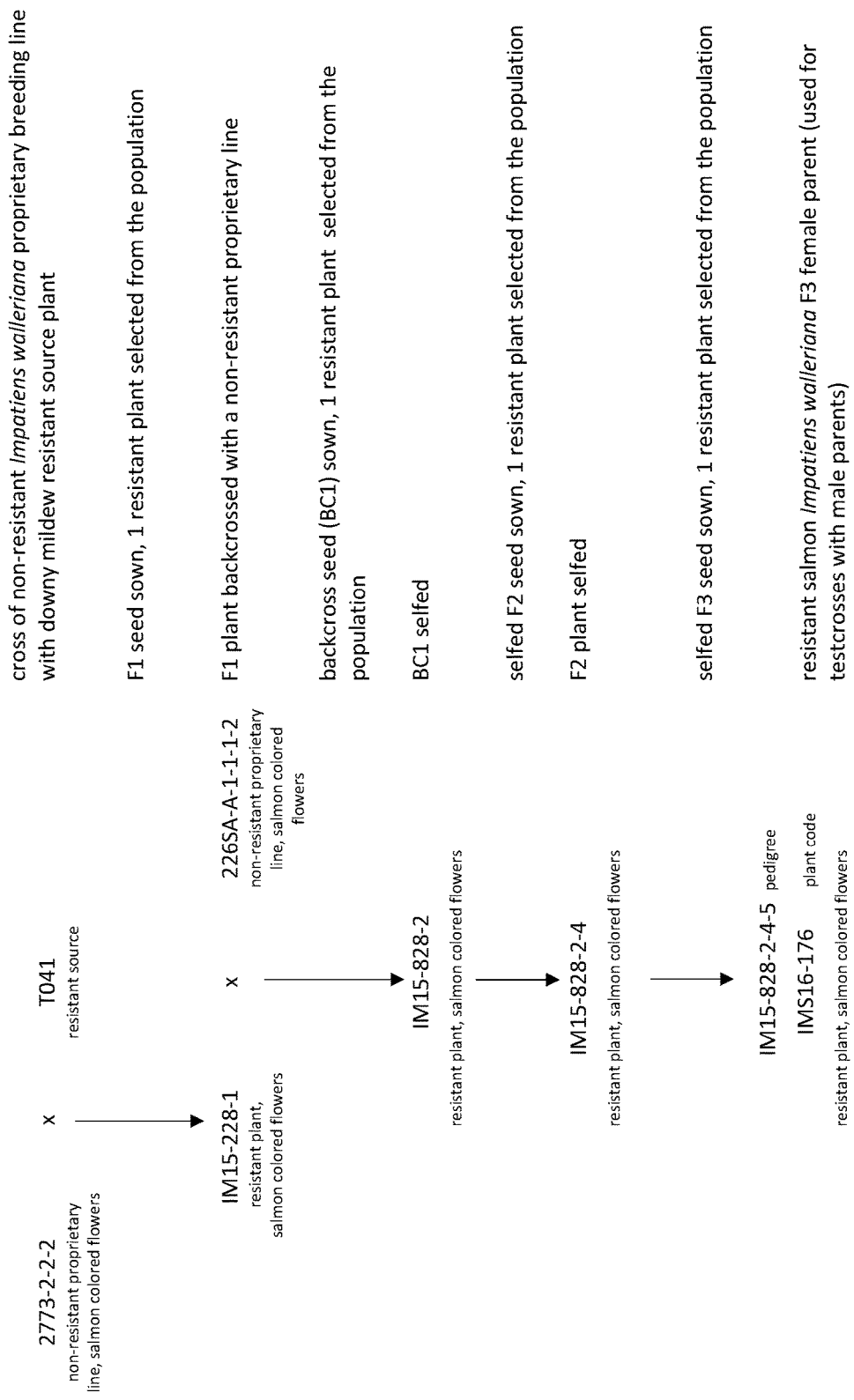
FIG. 6 shows a pedigree chart for IMS16-176 DMR *Impatiens* plant.
Figure 7:
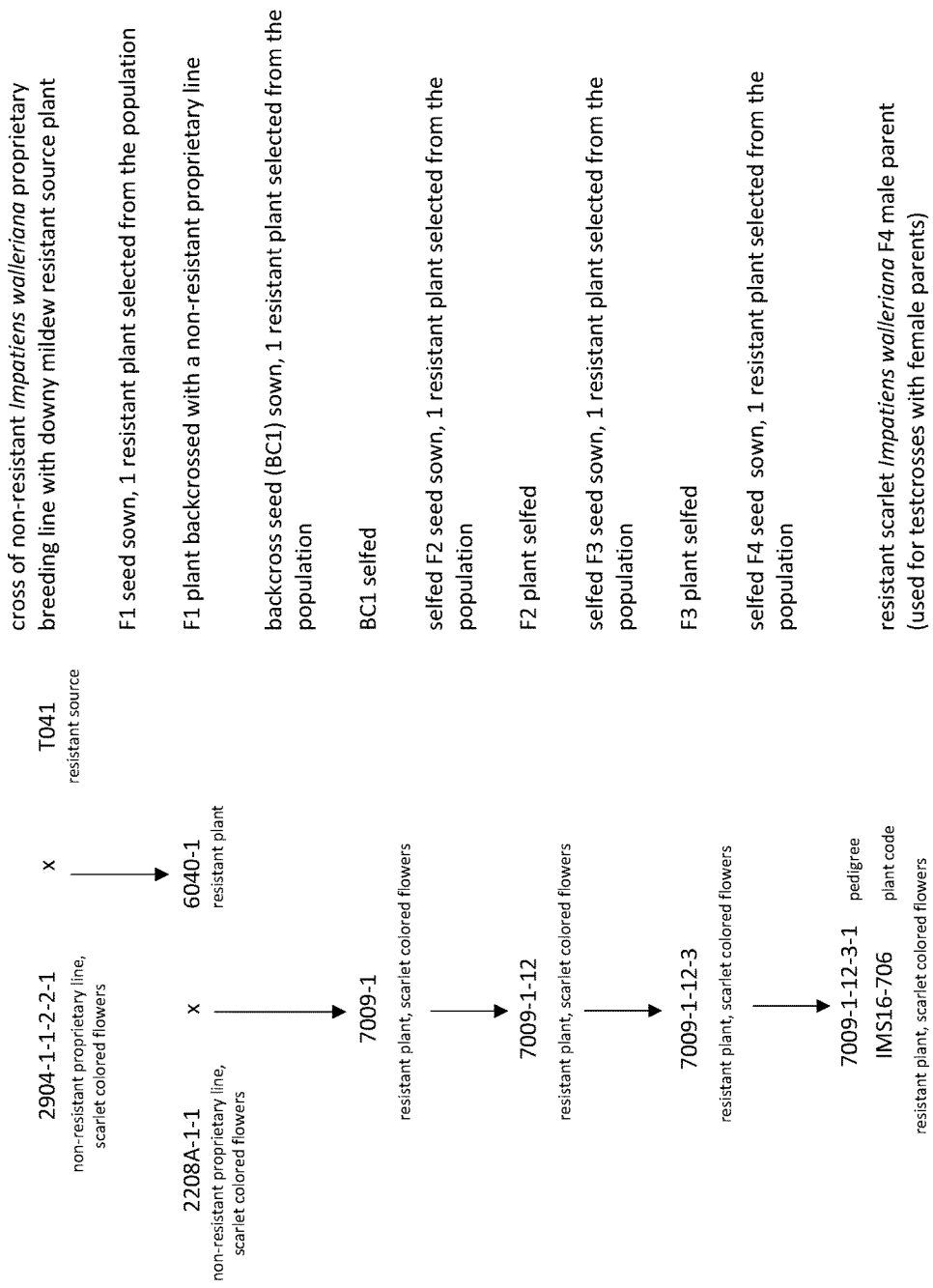
FIG. 7 shows a pedigree chart for IMS16-706 DMR *Impatiens* plant.
Figure 8:
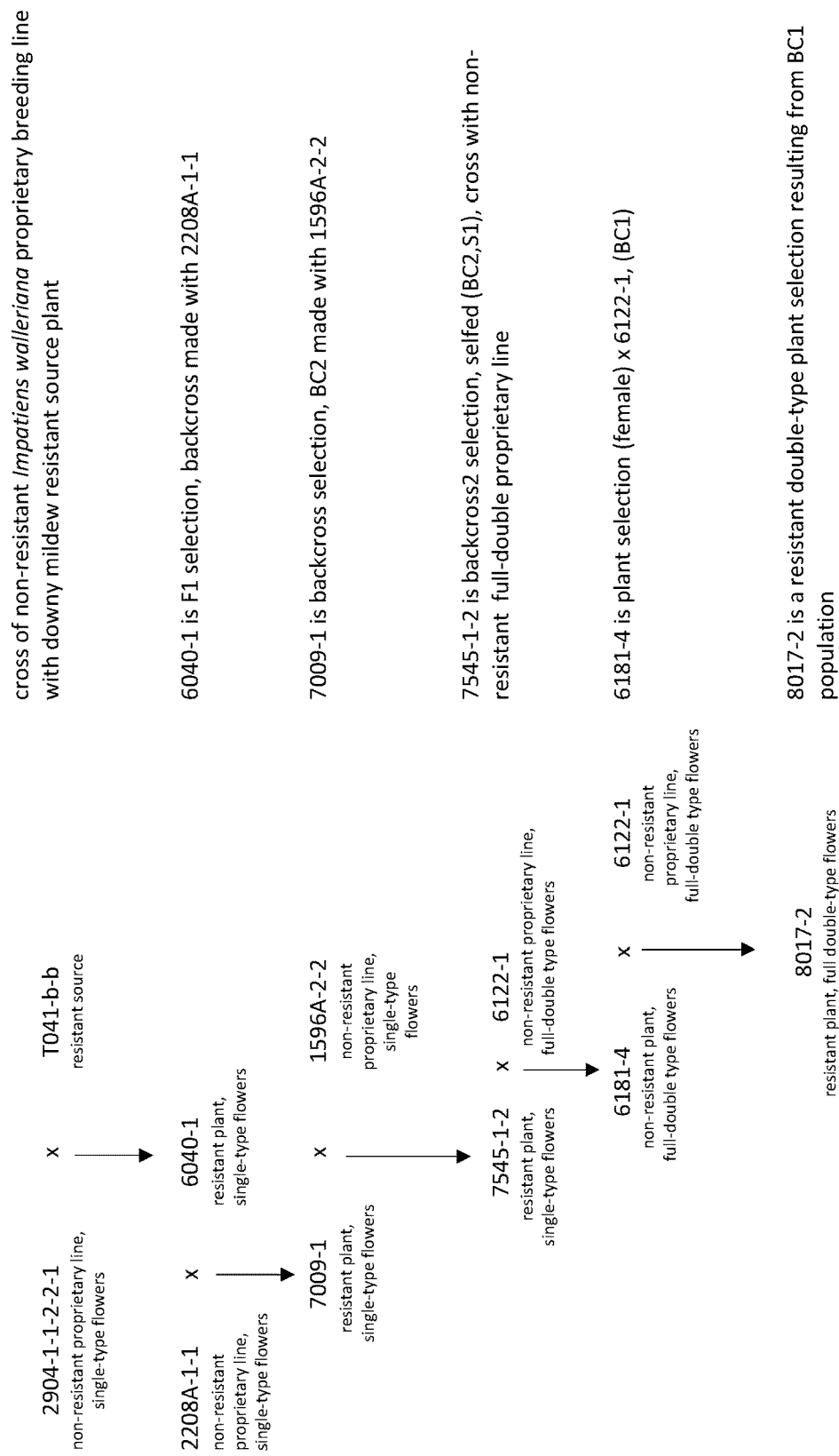
FIG. 8 shows a pedigree chart for double-type *Impatiens* plant 8017-2.
Figure 9:
FIG. 9 shows a pedigree chart for double-type *Impatiens* plant 6179-4.
Figure 10:
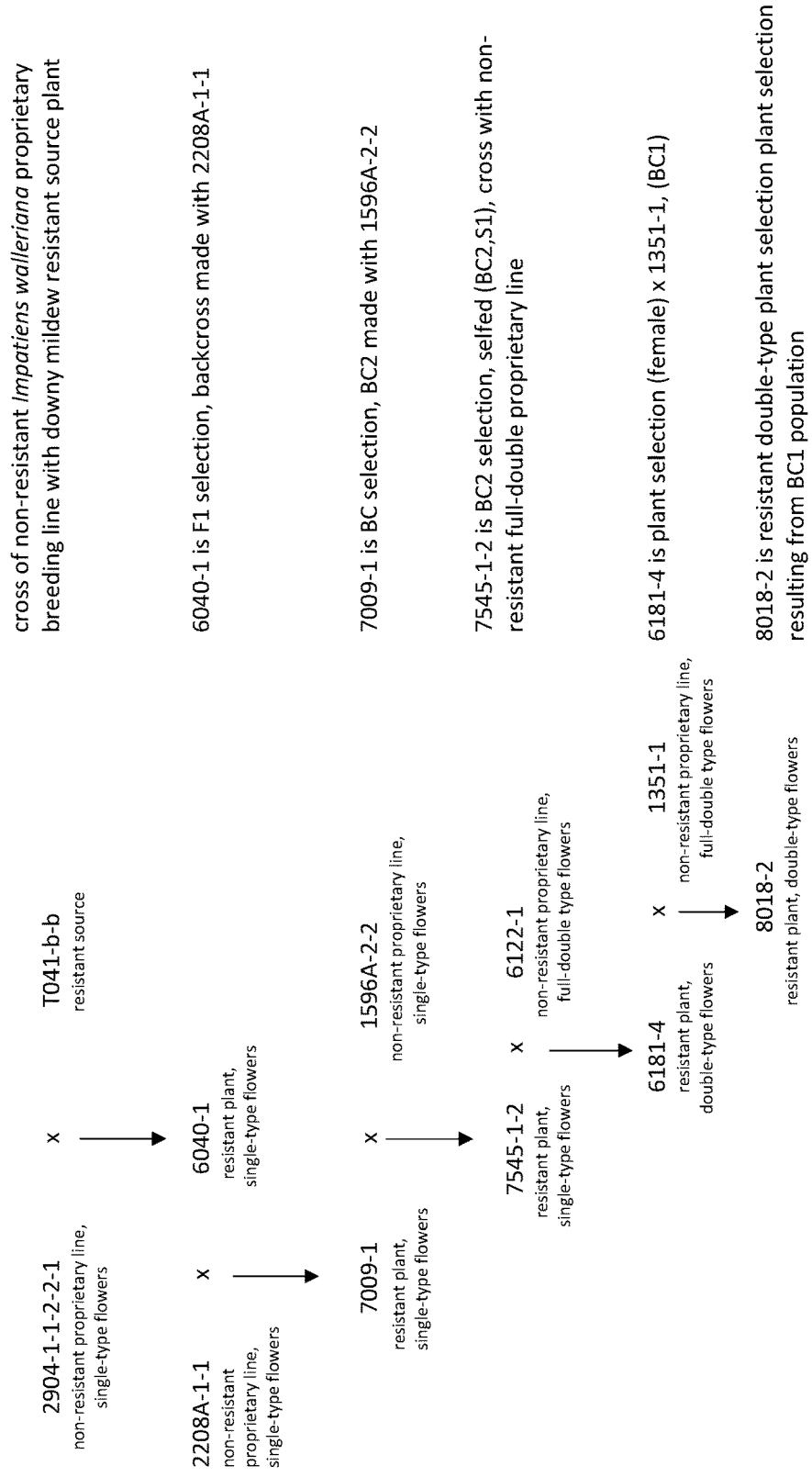
FIG. 10 shows a pedigree chart for double-type *Impatiens* plant 8018-2.

One aspect of the current disclosure concerns methods for producing seed of downy mildew resistant *Impatiens* plants as described herein. Alternatively, in other embodiments of the present disclosure, a downy mildew resistant *Impatiens* plant may be crossed with itself or with any second plant. Such methods can be used for propagation of downy mildew resistant (DMR) *Impatiens* plants or can be used to produce plants that are derived from the downy mildew resistant *Impatiens* plants disclosed herein. Plants derived from the downy mildew resistant *Impatiens* plants disclosed herein may be used, in certain embodiments, for the development of new *Impatiens* varieties.

The development of new varieties using one or more starting varieties is well known in the art. In accordance with the present disclosure, novel varieties may be created by crossing downy mildew resistant *Impatiens* plants followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Backcrossing can be used to improve a variety, and may be used, for example, to introduce a desired allele or trait into the plant genetic background of any plant that is sexually compatible with a plant of the present disclosure. Backcrossing transfers a specific desired trait from one inbred or non-inbred source to a variety that lacks that trait. This can be accomplished, for example, by first crossing a variety of a desired genetic background (recurrent parent) to a donor inbred (non-recurrent parent), which carries the appropriate allele or loci for the desired trait(s) in question. The progeny of this cross are then mated back to the recurrent parent, followed by selection in the resultant progeny for the desired trait to be transferred from the non-recurrent parent. The process is repeated, for example for five or more backcross generations with selection for the desired trait, until a plant is obtained wherein essentially all of the desired morphological and physiological characteristics of the recurrent parent are recovered in the converted plant, in addition to the single transferred locus from the nonrecurrent parent. The progeny thus have the characteristic being transferred, but are like the superior parent for most or almost all other loci. The last backcross generation can be selfed to give true-breeding progeny when the trait being transferred is introgressed into a true-breeding variety.

The recurrent parent therefore provides the desired genetic background, while the choice of the particular non-recurrent parent will depend on the purpose of the backcross. One of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele or an additive allele (between recessive and dominant) may also be transferred. In this instance it may be necessary to introduce a test of the progeny to determine if the desired characteristic has been successfully transferred.

Modified backcrossing may also be used with plants of the present disclosure. This technique uses different recurrent parents during the backcrossing. Modified backcrossing may be used to replace the original recurrent parent with a variety having certain more desirable characteristics or multiple parents may be used to obtain different desirable characteristics from each.

The plants of the present disclosure are particularly well suited for the development of new lines based on the genetic background of the plants. In selecting a second plant to cross with a downy mildew resistant *Impatiens* plant disclosed herein for the purpose of developing novel *Impatiens* lines, it will typically be preferred to choose those plants which either themselves exhibit one or more selected desirable characteristics or which exhibit the desired characteristic(s) when in hybrid combination. Examples of desirable traits may include, in specific embodiments, high flower yield, flower quality, high seed germination, seedling vigor, disease resistance, and adaptability for soil and climate conditions such as drought or heat. Consumer-driven traits, such as flower color, shape, and texture, even aroma and taste are other examples of traits that may be incorporated into new lines of *Impatiens* plants developed by this disclosure.

B. Further Embodiments of the Disclosure

In other embodiments, the present disclosure provides methods of vegetatively propagating a plant of the present disclosure. Such a method may comprise the steps of: (a) collecting tissue capable of being propagated from said plant; (b) cultivating said tissue to obtain proliferated shoots; and (c) rooting said proliferated shoots to obtain rooted plantlets. In other embodiments, such a method may further comprise growing downy mildew resistant *Impatiens* plants from the rooted plantlets. In still further embodiments, a plant of the present disclosure is propagated by seed, wherein a plant may be used as either a female or a male parent for producing progeny seed and plants.

Also provided are methods of producing a downy mildew resistant *Impatiens* plant of the present disclosure, said method comprising introgressing a desired allele from a plant comprising the allele into a plant of a different genotype. In certain embodiments, such an allele may be inherited from or introgressed from *Impatiens* sp. T041 or *Impatiens* sp. 7511, or a progeny or progenitor of any generation thereof comprising the allele. *Impatiens* sp. 7511 is a family of siblings created from self-crosses of *Impatiens* sp. T041, which comprises the genetic source for downy mildew resistance. The deposited *Impatiens* sp. 7511 seed has the downy mildew resistance trait from *Impatiens* sp. T041.

Many single locus traits have been identified that are not regularly selected for in the development of a new inbred but that can be improved by backcrossing techniques. Single locus traits may or may not be transgenic; examples of these traits include, but are not limited to, resistance to bacterial, fungal, or viral disease, or herbicide or insect resistance. These comprise genes generally inherited through the nucleus.

Direct selection may be applied where the single locus acts as a dominant trait. For this selection process, the progeny of the initial cross are assayed for viral resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of *Impatiens* plants for breeding is not necessarily dependent on the phenotype of a plant and instead can be based on genetic investigations. Thus, in one embodiment, the present disclosure provides the genetic complement of a downy mildew resistant *Impatiens* plant as described herein. "Genetic complement" as used herein refers to the aggregate of nucleotide sequences, the expression of which sequences defines the phenotype of, in the present case, a downy mildew resistant *Impatiens* plant, or a cell or tissue of that plant. A genetic complement thus represents the genetic makeup of a cell, tissue or plant, and a hybrid genetic complement represents the genetic make-up of a hybrid cell, tissue or plant. The genetic complement of a downy mildew resistant *Impatiens* plant as disclosed herein may be identified by any of the many well-known techniques in the art. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker-assisted selection.

Any other type of genetic marker or other assay which is able to identify the relative presence or absence of a trait of interest in a plant can also be useful for breeding purposes. Procedures for marker-assisted selection are well known in the art. Such methods will be of particular utility in the case of recessive traits and variable phenotypes, or where conventional assays may be more expensive, time consuming or otherwise disadvantageous. Types of genetic markers which could be used in accordance with the present disclosure include, but are not necessarily limited to, Simple Sequence Length Polymorphisms (SSLPs), Randomly Amplified Polymorphic DNAs (RAPDs; Williams et al., Nucleic Acids Res. 18:6531-6535:1990), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., Science 280:1077-1082, 1998).

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (Plant Physiology, 147: 969-977), for example, and elsewhere, provides a mechanism for integrating single or multiple traits or QTL into a line. This molecular breeding-facilitated movement of a trait or traits into a line or variety may encompass incorporation of a particular genomic fragment associated with a particular trait of interest into the line or variety by the mechanism of identification of the integrated genomic fragment with the use of flanking or associated marker assays. In the embodiment represented here, one, two, three or four genomic loci, for example, may be integrated into a line via this methodology. When this line containing the additional loci is further crossed with another parental line to produce hybrid offspring, it is possible to then incorporate at least eight separate additional loci into the hybrid. These additional loci may confer, for example, such traits as disease resistance, drought or heat tolerance, or a flower quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

C. Plants Derived by Genetic Engineering

Many useful traits that can be introduced by backcrossing, as well as directly into a plant, are those which are introduced by genetic transformation techniques. Genetic transformation may therefore be used to insert a selected transgene into a plant of the present disclosure or may, alternatively, be used for the preparation of transgenes which can be introduced by backcrossing. Methods for the transformation of plants that are well known to those of skill in the art and applicable to many plant species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the microprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable, and may be used to transform virtually any plant species.

Agrobacterium-mediated transfer is another widely applicable system for introducing gene loci into plant cells (Marton et al., Nature 277:129-131, 1978). An advantage of the technique is that DNA can be introduced into whole plant tissues, thereby bypassing the need for regeneration of an intact plant from a protoplast. Modern Agrobacterium transformation vectors are capable of replication in E. coli as well as Agrobacterium, allowing for convenient manipulations (Nester et al., Basic Life Sci. 30:815-822, 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, Agrobacterium containing both armed and disarmed Ti genes can be used for transformation.

In those plant strains where Agrobacterium-mediated transformation is efficient, it is the method of choice because of the facile and defined nature of the gene locus transfer. The use of Agrobacterium-mediated plant integrating vectors to introduce DNA into plant cells is well known in the art (Fraley et al., Plant Mol. Biol. 3:371-378, 1984; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., Mol. Gen. Genet. 199:183-188, 1985; Omirulleh et al., Plant Mol. Biol. 21:415-428, 1993; Fromm et al., Nature 312:791-793, 1986; Uchimiya et al., Mol. Gen. Genet. 204:204, 1986; Marcotte et al., Nature 335:454, 1988). Transformation of plants and expression of foreign genetic elements is exemplified in Choi et al. (Plant Cell Rep. 13: 344-348, 1994), and Ellul et al. (Theor. Appl. Genet. 107:462-469, 2003).

A number of promoters have utility for plant gene expression for any gene of interest including, but not limited to, selectable markers, scoreable markers, genes for pest tolerance, disease resistance, or any other gene of agronomic interest. Examples of constitutive promoters useful for plant gene expression include, but are not limited to, the cauliflower mosaic virus (CaMV) P-35S promoter, which confers constitutive, high-level expression in most plant tissues (see, e.g., Odel et al., Nature 313:810, 1985), including in monocots (see, e.g., Dekeyser et al., Plant Cell 2:591, 1990; Terada and Shimamoto, Mol. Gen. Genet. 220:389, 1990); a tandemly duplicated version of the CaMV 35S promoter, the enhanced 35S promoter (P-e35S); the nopaline synthase promoter (An et al., Plant Physiol. 88:547, 1988); the octopine synthase promoter (Fromm et al., Plant Cell 1:977, 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem; the cauliflower mosaic virus 19S promoter; a sugarcane bacilliform virus promoter; a *commelina* yellow mottle virus promoter; and other plant DNA virus promoters known to express in plant cells.

A variety of plant gene promoters that are regulated in response to environmental, hormonal, chemical, and/or developmental signals can also be used for expression of an operably linked gene in plant cells, including promoters regulated by (1) heat (Callis et al., Plant Physiol. 88:965-968, 1988), (2) light (e.g., pea rbcS-3A promoter, Kuhlemeier et al., Plant Cell 1:471-478, 1989; maize rbcS promoter, Schaffner and Sheen, Plant Cell 3:997-1012, 1991; or chlorophyll a/b-binding protein promoter, Jones et al., EMBO J. 4:2411-2418, 1985), (3) hormones, such as abscisic acid (Marcotte et al., Plant Cell 1:969-976, 1989), (4) wounding (e.g., wun1, Siebertz et al., Plant Cell 1:961-968, 1989); or (5) chemicals such as methyl jasmonate, salicylic acid, or Safener. It may also be advantageous to employ organ-specific promoters (e.g., Chen et al., Genetics 116:469-477, 1987; Schernthaner et al., EMBO J. 7:1249-1255, 1988; Bustos et al., Plant Cell 1:839-853, 1989).

Exemplary nucleic acids which may be introduced to plants of this disclosure include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a downy mildew resistant *Impatiens* plant according to the present disclosure. Non-limiting examples of particular genes and corresponding phenotypes one may choose to introduce into a downy mildew resistant *Impatiens* plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to Agrobacterium strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or co-suppression-mediated mechanisms (see, for example, Bird et al., Biotechnol. Genet. Eng. Rev. 9:207-227, 1991). The RNA could also be a catalytic RNA molecule (i.e., a ribozyme) engineered to cleave a desired endogenous mRNA product (see for example, Gibson and Shillitoe, Mol. Biotechnol. 7:125-137, 1997). Thus, any gene which produces a protein or mRNA which expresses a phenotype or morphology change of interest is useful for the practice of the present disclosure.

D. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid (F1), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

F1 Hybrid: The first generation progeny of the cross of two non-isogenic plants.

Genotype: The genetic constitution of a cell or organism.

Haploid: A cell or organism having one set of the two sets of chromosomes in a diploid.

Hybrid: F1 progeny produced from crossing two non-identical parental lines. Parental lines may be related or unrelated. In accordance with the present disclosure, a "hybrid" may refer to Impatiens plants comprising downy mildew resistance as described herein.

Inbred Line: A group of genetically and phenotypically similar plants reproduced by inbreeding.

Linkage: A phenomenon wherein alleles on the same chromosome tend to segregate together more often than expected by chance if their transmission was independent.

Phenotype: The detectable characteristics of a cell or organism, which characteristics are the manifestation of gene expression.

Plant Part: As used herein, a plant part refers to a part of a plant of the present disclosure. A plant part may be defined as comprising a cell of such plant, such as a cutting, a leaf, a floret, an ovule, pollen, a cell, a seed, a flower, an embryo, a meristem, a cotyledon, an anther, a root, a root tip, a pistil, a stalk, a stem, and a protoplast or callus derived therefrom.

Quantitative Trait Loci (QTL): Quantitative trait loci (QTL) refer to genetic loci that control to some degree numerically representable traits that are usually continuously distributed.

Regeneration: The development of a plant from tissue culture. In accordance with the present disclosure, a regenerated Impatiens plant as described herein would comprise a downy mildew resistance allele that confers downy mildew resistance.

Resistance: The ability of an Impatiens variety to restrict the growth and development of downy mildew or the damage it causes when compared to susceptible Impatiens varieties under similar environmental conditions and pressure from downy mildew. Resistant Impatiens varieties may exhibit some disease symptoms or damage under heavy pressure from downy mildew.

Self-pollination or self-fertilization: The transfer of pollen from the anther to the stigma of the same plant. A "self-pollinated" or "self-fertilized" seed refers to a seed arising from fusion of male and female gametes produced by the same plant. In hybrid seed production, self-pollinated or self-fertilized seed refers to that portion (e.g., less than 1%) of the seed that was the result of self-pollination.

Single Locus Converted (Conversion) Plant: Plants which are developed by a plant breeding technique called backcrossing, wherein essentially all of the desired morphological and physiological characteristics of an Impatiens variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Susceptibility: The inability of an Impatiens variety to restrict the growth and development of downy mildew.

Tissue Culture: A composition comprising isolated cells of the same or a different type or a collection of such cells organized into parts of a plant. A tissue culture in accordance with the present disclosure may originate from or comprise cells or protoplasts from a plant part selected from the group consisting of embryos, meristems, cotyledons, pollen, leaves, anthers, roots, root tips, pistil, flower, florets, seed, stems, and protoplasts or callus derived therefrom.

E. Deposit Information

A deposit of Impatiens sp. 7511, disclosed above and recited in the claims, has been made with the American Type Culture Collection (ATCC), 10801 University Blvd., Manassas, Va. 20110-2209. The date of the deposit was Jan. 26, 2017. The accession number for those deposited seeds of Impatiens sp. 7511 is ATCC Accession Number PTA-123803. Upon issuance of a patent, all restrictions upon the deposits will be removed, and the deposits are intended to meet all of the requirements of 37 C.F.R. § 1.801-1.809. The deposits will be maintained in the depository for a period of 30 years, or 5 years after the last request, or for the effective life of the patent, whichever is longer, and will be replaced if necessary during that period.

Impatiens sp. 7511 is a family of siblings created from self-crosses of Impatiens sp. T041 (see below). The deposited Impatiens sp. 7511 seed has the downy mildew resistance trait from Impatiens sp. T041.

EXAMPLES

Although the foregoing disclosure has been described in some detail by way of illustration and example for purposes of clarity and understanding, it will be obvious that certain changes and modifications may be practiced within the scope of the present disclosure, as limited only by the scope of the appended claims.

Example 1

Origin of Downy Mildew Resistant *Impatiens*

Self-crosses from a Ball Horticultural Company proprietary *Impatiens* germplasm collection were screened for downy mildew resistance. One *Impatiens* sp. selection identified as T041 was found to be highly resistant to downy mildew and exhibited both lower disease incidence and severity when compared to the susceptible *I. walleriana* control and to other *Impatiens* sp. in the germplasm screen.

Four week old seedlings were spray-inoculated with a suspension of *Plasmopara obducens* sporangia (1.0×105 sporangia/ml). The isolate of *P. obducens* used for inoculations was obtained from naturally infected *Impatiens walleriana* plants growing in an outdoor field trial in Holland in August 2012 and subsequently established and maintained on seed-raised *I. walleriana* in a laboratory growth chamber. Inoculum was prepared by rinsing sporulating *impatiens* leaves in water with a drop of Tween 20. The sporangial suspension was passed through 4 layers of cheesecloth to remove mycelial fragments. Using an airbrush sprayer attached to an air compressor, the sporangial suspension was applied to adaxial and abaxial leaf surfaces as a fine mist. Plants were immediately bagged after inoculation to maintain 100% relative humidity and placed into a 17° C., dark growth chamber overnight resuming a 23° C. days and 17° C. nights and 12 hr light/dark schedule the following morning. Plants were evaluated 14 days after inoculation. The total number of leaves per plant, the number of leaves or cotyledons with visible sporulation and the degree of sporulation, the number of leaves with internal gray discoloration and the number of abscised leaves and cotyledons was recorded.

All 24 inoculated plants of T041 exhibited resistance to the pathogen. Each plant had an average of 26 leaves, of which 18 plants had no visible leaf sporulation, 6 plants had 1 attached or abscised cotyledon or leaf with sparse leaf sporulation, and 9 plants had 1 or 2 leaves with internal gray discoloration but no sporulation. In comparison, the susceptible *Impatiens walleriana* SUPER ELFIN 'White' control had heavy sporulation on the abaxial surface of >90% of the leaves of each plant, as did some of the other *Impatiens* sp. selections.

Example 2

*Impatiens* Seedling Assay for Resistance to Downy Mildew

*Plasmopara obducens* causes downy mildew of *Impatiens*. A seedling assay was designed to test for resistance in impatiens against this obligate parasite. The assay is conducted in a greenhouse under controlled environmental conditions.

*Impatiens* seeds were sown into 128 cell plug trays filled with a peat-based, soilless potting mix. Trays were placed in a 25° C. mist chamber with continuous light (ca. 50 micromol/s) for approximately 4 to 6 days. Trays were transferred to an enclosed greenhouse and maintained at approximately 20° C. average day temperature with 14 hours of light per day (ca. 50 micromol/s light).

The three week old seedlings were inoculated with a suspension of *P. obducens* sporangia (ca. 1×105 sporangia/ml). The isolate of *P. obducens* used for inoculations was obtained from naturally-infected *Impatiens walleriana* plants grown in an outdoor field trial in Holland and subsequently maintained on *I. walleriana* plants enclosed in plastic bags and grown in a greenhouse. Inoculum was prepared by vigorously rinsing sporulating *impatiens* leaves in water. After adjusting the concentration, the sporangial suspension was applied to leaves of the seedlings using a hand-pump spray bottle. Each tray was transferred into a clear plastic bag, tied closed to maintain 100% humidity and placed in the dark for 18 hours at 17° C.

The bags were removed and trays were transferred back to the lighted greenhouse and maintained at approximately 20° C. average day temperature with 14 hour days. Relative humidity was approximately 60 to 75% and seedlings were watered through sub-irrigation to reduce free water on the leaves. After 10 to 14 days, trays were placed back into the clear plastic bags to promote sporulation. The bagged trays were maintained in the greenhouse for two to four days at which time the bags were removed and the seedlings were evaluated and rated a second time for signs of downy mildew infection.

Seedlings were visually evaluated for visible sporulation on the abaxial leaf surfaces as well as for internal leaf discoloration. Seedlings were rated on a scale of 1-4 based on the incidence and severity of the disease as described below in Table 1.

TABLE 1

Rating Scale for Disease Incidence and Severity

| Rating Scale | Description of Category |
|---|---|
| 1 | >2 leaves, both young and fully-mature, with moderate to heavy sporulation |
| 2 | sparse sporulation on 1-2 leaves |
| 3 | leaf discoloration but no sporulation |
| 4 | no sporulation |

Seedlings rated 2 through 4 were transplanted into 9-cm pots filled with soilless potting mix and placed back into the greenhouse for 14 days and grown using standard practices known to those skilled in the art. After 14 days plants were transferred back into individual clear plastic bags to increase the humidity to 100% and promote sporulation for a second time. After two days, plants were removed from the bags and evaluated using the rating scale previously described in Table 1. Plants rated 3 or 4 were maintained for use in the breeding program, and those rated 1 or 2 were discarded.

Example 3

Inheritance of Downy Mildew Resistance

A Ball Horticultural Company proprietary *Impatiens* sp. breeding line coded T041-1-B-50 was crossed as the female parent with a Ball Horticultural Company proprietary *Impatiens walleriana* inbred breeding line coded G0008Q as the male parent. The F1 population was screened for downy mildew resistance as described in Example 2 and rated as highly resistant. One F1 plant coded IMC-211 was selected and self-crossed. The resulting F2 population was screened for downy mildew resistance, and plant ratings were as follows: 9/16 High Resistance; 3/16 Moderate Resistance, 3/16 Low Resistance, and 1/16 No resistance.

The resistant phenotype is characterized as plants at 14 to 30 days after inoculation exhibiting no or sparse sporulation and/or internal discoloration of the leaf tissue of one or two leaves. Plants without resistance are characterized at 14 to 30 days after inoculation as having leaf yellowing, dense sporulation on the abaxial leaf surfaces, extensive leaf abscission and eventual collapse of the plant.

Example 4

Introgression of Downy Mildew Resistance into *Impatiens walleriana*

*Impatiens* sp. selection T041 was used in an introgression breeding program to introduce genetic downy mildew resistance into *Impatiens walleriana*. Individual plants selected from the method, as described in Example 2, are listed below in Table 2. All resistant plants have selection T041 *Impatiens* sp. in their pedigree.

TABLE 2

Identification of Plants Having Resistant Phenotypes

| Plant Code | Female Parent | Male Parent | Conclusion |
|---|---|---|---|
| 6069-1 | 2494A-1 | T041 | Resistant F1 plant |
| 6068-2 | 1532A-1-1-1-1 | T041 | Resistant F1 plant |
| IM15-733-1 | 1532A-1-1-1-1 | 6068-2 | Resistant BC plant |
| IM15-733-1-2 | IM15-733-1 | IM15-733-1 | Resistant F2 plant |
| IM15-905-2-5 | IM15-905-2 | IM15-905-2 | Resistant F2 plant |
| IM15-0122-1-1-04-2 | IM15-0122-1-1-04 | IM15-0122-1-1-04 | Resistant F4 plant |

Pedigrees illustrating the introgression of genetic downy mildew resistance from *Impatiens* sp. selection T041 into *Impatiens walleriana* are shown in FIGS. 1 through 10. Breeding examples include introgression of the resistance into multiple colors of standard commercial *Impatiens walleriana* and introgression of the resistance into multiple double-flowered breeding lines.

The downy mildew resistant *Impatiens walleriana* female and male parents were utilized in crosses to develop at least the F1 hybrids shown in Table 3, below.

TABLE 3

| Flower Color | Hybrid Breeder ID | Female Parent | Male Parent |
|---|---|---|---|
| white | IM16-771 | IMS16-675 | IMS16-730 |
| orange | IM17-748 | IMS17-514 | IMS17-578 |
| salmon | IM17-453 | IMS17-176 | IMS16-555 |
| deep salmon | IM17-452 | IMS17-176 | IMS16-706 |

Example 5

Marker Development for Downy Mildew Resistance in *Impatiens walleriana*

To develop markers for T041 mediated Downy Mildew Resistance in *Impatiens*, mapping populations were developed in *Impatiens*. Resistant parental lines (25) were chosen on the basis of disease response in the seedling assay. One susceptible parental line was chosen as the other parent (G0008Q). Crosses between the 25 resistant lines and the susceptible line resulted in 25 independent F1's, that were selfed to produce 25 F2 mapping populations. All F1's and small F2 populations were evaluated for the disease response, and on the basis of the segregation pattern one population was chosen for the initial mapping of the disease resistance locus and for marker development (IMC243).

The mapping population used for marker development (IMC243) consisted of 70 F2 individuals. For marker validation also a germplasm panel was included, consisting of 74 samples, including 4 parental lines and 3 F1 hybrids in duplicate. Leaf samples from population IMC243 were collected before disease assays were started, leaf samples from germplasm were collected from a greenhouse. For this material disease resistance scores were communicated as qualitative scores (Resistant or Susceptible). The leaf samples were used for the isolation of DNA and for subsequent SBG genotyping.

The panel of 144 samples was used for the preparation of SBG libraries with PstI/MseI as the enzyme combination with two selective nucleotides added to the primers (+0/+GT). The libraries were subsequently sequenced in 4 lanes of the Illumina HiSeq (single read sequencing). After sequencing Illumina reads were filtered on the basis of quality, presence of sample identification tags and the PstI restriction site motif. Subsequently, reads from all samples were used to generate a reference sequence and the produced clusters were mined for SNPs. In this step also a preliminary genotype score file was constructed.

After Sequence Based Genotyping (SBG), genotypic data of samples of IMC243 and their parental lines was selected from the total dataset as the dataset that was used for mapping. For this dataset markers were selected that were segregating as expected for an F2 mapping population.

In total, 2755 markers showed F2-type segregation and were used in the construction of a genetic map using Keygene proprietary software CarteBlanche. First the markers were assigned to linkage groups based on recombination frequencies. Next the order of the markers was estimated in multiple rounds and a "best map" was extracted. Finally a check for inconsistencies was performed. As a result, in total 2732 markers were mapped into 9 major (>100 markers) and 2 minor (<20 markers) linkage groups. A summary of the genetic map is presented in Table 4.

TABLE 4

Summary of the Genetic Map

| Name | # Loci | Length (cM) |
|---|---|---|
| Group-I | 551 | 216.4 |
| Group-II | 409 | 216.9 |
| Group-III | 337 | 146.4 |
| Group-IV | 310 | 163.1 |
| Group-V | 288 | 140 |
| Group-VI | 235 | 136.3 |
| Group-VII | 231 | 115.4 |
| Group-VIII | 187 | 109.8 |
| Group-IX | 149 | 110.7 |
| Group-X | 19 | 11.7 |
| Group-XI | 16 | 47.9 |
| Total | 2732 | 1414.6 |

For population IMC243 disease response data were collected from single F2 plants on 5 dates according to a modified version of the protocol described in Table 1. Seedlings were rated on a scale of 0 to 5, with 0 being just the stem left or a dead plant, 1 being major leaf drop, and the plant near collapse, 2 being some leaf drop and/or yellowing, 3 being major sporulation, with the plant still appearing well, 4 being minor sporulation, and a healthy looking plant, and 5 being no sporulation. Disease development in the F2 individuals over time was monitored. Data collected on different dates were considered as separate traits. The overall mean over the 5 dates was also determined and used as trait. Subsequently, correlations between the traits were estimated and are presented in Table 5. A strong correlation was observed between the traits of the final three dates, and of the trait representing the overall mean.

TABLE 5

Correlations Between the Traits

|  | T19-12 | Tmean_22-12 | Tmean27-12 | Tmean_30-12 | Tmean_02-01 | Toverall_mean |
|---|---|---|---|---|---|---|
| T19-12 |  |  |  |  |  |  |
| Tmean_22-12 | 0.61 |  |  |  |  |  |
| Tmean27-12 | 0.26 | 0.44 |  |  |  |  |
| Tmean_30-12 | 0.21 | 0.46 | 0.86 |  |  |  |
| Tmean_02-01 | 0.22 | 0.45 | 0.81 | 0.95 |  |  |
| Toverall_mean | 0.46 | 0.65 | 0.89 | 0.94 | 0.94 |  |

A QTL mapping was performed using the data of the six traits individually and the genotypic data of the IMC243 population. QTL were identified for all traits on Linkage Group 2 (LG2) and/or Linkage Group 5 (LG5). The QTL on LG5 was observed in the early stages of disease development and the QTL on LG2 was observed during the later stages of disease development when also a clear separation between susceptible and resistant individuals was observed. Since there was little correlation between the early response QTL and the later response QTL the later QTL seemed more meaningful. Therefore, the correlation between genotype and phenotype was investigated for the LG2 QTL region.

The association of the LG2 QTL region with the disease response at timepoints 3, 4 and 5 was recorded. It was observed that disease scores 1 and 2 (indicative for susceptibility) were highly associated with Balleles, disease scores 4 and 5 were highly associated with A or H alleles, disease scores 3 were most frequently observed associated with H-scores. Therefore it was concluded that the T041 resistance gene mapped on LG2 around 75 cM. Since the number of individuals in the F2 population and therefore the number of recombinations was limited, the T041 gene could not be more precisely positioned among the available markers.

The germplasm panel consisted of 67 samples, including 4 parental lines (T041-1-B50 alias TP25-1, T041-1-B3 alias TP3-2, T041-1-B4 alias TP4-2 as resistant lines, G0008Q alias TP26-1 and their 3 F1 hybrids TF1-24B, TF1-3B and TF1-4B, respectively). For the germplasm samples, disease resistance scores were communicated as qualitative scores (Resistant or Susceptible). For the association analysis only the mapped markers were selected from the total dataset. In addition, filtering was done for <10% missing data and <90% Major Allele Frequency, resulting 2424 mapped markers in the data set for association analysis.

Two clearly associated regions were identified, on LG2 and on LG4. Interestingly, LG2 was overlapping with the identified region in the QTL mapping. LG4 was not found associated with disease resistance in the QTL mapping, and the LG5 region identified in the QTL mapping was not confirmed in the association analysis. It was also observed that several markers were not present in the association analysis that were present in the region of interest on the basis of the genetic mapping. Those markers were retrieved from the original dataset and it turned out that they had been removed from the dataset for association mapping on the basis of % U-scores. Clearly the marker alleles were amplified in the resistant germplasm, however not in the susceptible germplasm. These markers were subsequently integrated in the dataset for association analysis using the marker order in the genetic map.

The association of the markers in the LG2 QTL region with the disease response (Resistant or Susceptible) was examined. Again the region around 75 cM was most clearly associated with resistance, and markers in this area showed 100% association with the disease response phenotype.

Nine markers were selected in the T041 resistance associated region on chromosome 2 on the basis of the genetic map and were converted to KASPar markers. Names and position of the markers are provided in Table 6, SNP sequences are provided in Table 7. Markers were selected for two purposes: 1) Validation of markers to select for T041 mediated resistance; 2) Validation of markers at the borders of the best associated region to select for recombinants in the region as part of the T041 gene isolation project.

TABLE 6

Overview of the SNPs Selected for Validation as KASPar Assays

| # | SBG marker | cM position |
|---|---|---|
| SNP8 | 16090187_Impatience_SBG_365004_60 | 663 |
| SNP3 | 16090187_Impatience_SBG_285385_35 | 69.4 |
| SNP6 | 16090187_Impatience_SBG_353380_68 | 75.1 |
| SNP5 | 16090187_Impatience_SBG_298705_40 | 75.2 |
| SNP4 | 16090187_Impatience_SBG_1494592_69 | 75.3 |
| SNP1 | 16090187_Impatience_SBG_1295214_40 | 75.8 |
| SNP7 | 16090187_Impatience_SBG_282803_70 | 77.7 |
| SNP9 | 16090187_Impatience_SBG_232915_83 | 77.9 |
| SNP2 | 16090187_Impatience_SBG_1469463_50 | 80.3 |

TABLE 7

KASPar Markers with Their Sequence and SNP

| SNP # | SBG Marker | SNP Sequence (SNP in brackets) |
|---|---|---|
| 1 | 16090187_Impatience_SBG_1295214_40 | CCAACCTTTCACTCAGCCGTCTGTTTCCATATCCTCATG[C/T]GGCTTCGATGAACTATCCATCGGTAGCTCAAAATGCTCCGCTATTACCCTCTTYGGTTTTAGGCWGCTAACAGA (SEQ ID NO: 1) |
| 2 | 16090187_Impatience_SBG_1469463_50 | AACGACGCGTGGCCGAAGCCCTCGAGCGAGCGCGAACATACCAAGTCCT[C/T]AGAGCGAACGAGGCCGAGTTCGAAGTGATATCTCACGAGGGAACCCACGTCGTGGATATMCGTA (SEQ ID NO: 2) |

TABLE 7-continued

KASPar Markers with Their Sequence and SNP

| SNP # | SBG Marker | SNP Sequence (SNP in brackets) |
|---|---|---|
| 3 | 16090187_Impatience_SBG_285385_35 | ACAATGGTTTGACTGTCGTAGTYGGTGGAGGAGC GCAATTGCAGCCCATGGATCATCGCTATCC AMWGAAGGGGGGATGCTTTTTGGGATCAATGGTCT TGATGTTGATTTCG (SEQ ID NO: 3) |
| 4 | 16090187_Impatience_SBG_1494592_69 | TGACCAATACATCACTTGAAAATGTTATGTTAGTG GAAGATATGTTCATGAAATCTTCTAAAGAGAGT [G/T]TAGTTTCTTGGAACGTGATGATTTCTGTCT ACTTGAAGAATTCCC (SEQ ID NO: 4) |
| 5 | 16090187_Impatience_SBG_298705_40 | TGTGGTATTTGGAGATGCTCTTAGTGGTTGTAAG GCGGG[A/T]GCAGGTTGTCCTTACGCTGTTACTT ACGGAGATGGGAGCTCGACTTCTGGACATTTTGTG AAGGATATCGTACA (SEQ ID NO: 5) |
| 6 | 16090187_Impatience_SBG_353380_68 | TTCAAGCTGCCATTCTGTGTGGGGAGGGAAATCC ACAAGTGCGAGACCTTGTGCTTCTCGATGTCAC [A/T]CCTCTGTCTCTTGGARTTKATRTACTTGGA GGCATTATGTCAGTGT (SEQ ID NO: 6) |
| 7 | 16090187_Impatience_SBG_282803_70 | ACAGTTATAGCTTAGGGTAGAAACTTCGGGAGAGA CGGAGAGATGGGGGCCAAACTCACAAGCAATGGA [C/G]GAAGCATTGGAAGGGAGGAGAGAAGATGGG TTATTGGGAGATGG (SEQ ID NO: 7) |
| 8 | 16090187_Impatience_SBG_365004_60 | TTCGAYCATCCTCTGTTGCAAAAGAGCAATCGCGC CGATGCATCCGTAAACAGGATCGC[T/C]GAGCCT GACCTCAGCCTGGAATACGAGAGAGTTGACGGCGT CTRYGCGGCGATC (SEQ ID NO: 8) |
| 9 | 16090187_Impatience_SBG_232915_83 | KTTCAGGGACAGACGATTTTGGGCCGTGCCCTCTA TCAGAAGCGAACCGCATACAGATTGGAGTTGACGT CGAAGAGGGGG[A/G]TCTTGGATAAGTGTGACTT CTTCCGGTGAAG (SEQ ID NO: 9) |

The nine KASPar markers were validated on the same panel of samples. Besides the germplasm also three times 16 F2 individuals were included from mapping populations IMC222, IMC223, and IMC243 respectively. Results for a subset of the susceptible germplasm and all resistant germplasm were examined next to the original genotyping results using SBG.

The following conclusions were drawn from the validation analysis: 1) All KASPar assays showed genotyping results similar to the earlier SBG results; For SNP1, for which U-scores were observed as SBG marker, A-scores were observed as KASPar marker like in the resistant germplasm; 2) Two markers SBG_1295214_40 (SNP5) and SBG_1494592_69 (SNP4) showed best association with the phenotype, like the original SBG marker: these markers are currently the best diagnostic markers; 3) SNPs 6, 1, 9 and 2 are informative in the mapping populations, however not in the germplasm, since they do not distinguish between susceptible and resistant material; 4) All markers were polymorphic between the parental lines (P25_1 and P26_1) of the used mapping population IMC243. Interestingly, one resistant parental line (P3_2) is not polymorphic with the susceptible parent P26_1 for SNP8, indicating that this marker is outside the R-gene region: it was also observed that indeed SNP8 was not segregating in population IMC222; 5) Three mapping populations have been selected for the screening of recombinants in the current T041 studies: populations IMC243 (P25×P26), IMC222 (P3×P26) and IMC 223 (P4×P26). As flanking markers for the screening of recombinants SNP 8 and 2 were selected for populations IMC243 and IMC223, SNP 3 (instead of SNP 8, since not polymorphic) and 2 for population IMC222. As best marker to test for presence of T041 SNP 5 was selected; 6).

The use of the term "or" in the claims is used to mean "and/or" unless explicitly indicated to refer to alternatives only or the alternatives are mutually exclusive, although the present disclosure supports a definition that refers to only alternatives and to "and/or." When not used in conjunction closed wording in the claims or specifically noted otherwise, the words "a" and "an" denote "one or more."

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has" or "includes" one or more steps is not limited to possessing only those one or more steps and also covers other unlisted steps. Similarly, any cell that "comprises," "has" or "includes" one or more traits is not limited to possessing only those one or more traits and covers other unlisted traits.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the present disclosure. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the present disclosure as defined by the appended claims.

What is claimed is:

1. An *Impatiens walleriana* plant of a cultivated variety comprising in its genome an introgressed locus that confers resistance to downy mildew relative to a wild type plant, wherein said locus comprises SEQ ID NO:4 or SEQ ID NO:5, and wherein a representative sample of seed comprising said locus has been deposited under ATCC Accession No. PTA-123803.

2. The plant of claim 1, wherein the plant is inbred.

3. The plant of claim 1, wherein the plant is hybrid.

4. A plant part of the plant of claim 1, wherein the plant part comprises at least one cell of said plant.

5. The plant part of claim 4, further defined as a cutting, leaf, pollen, a meristem, a cell, a seed, or an ovule.

6. A seed that produces the plant of claim 1.

7. A method of producing a downy mildew resistant *Impatiens* seed, the method comprising crossing the plant of claim 1 with itself or a second *Impatiens* plant.

8. The method of claim 7, further defined as comprising crossing the plant with a second, distinct *Impatiens* plant to produce an F1 hybrid *Impatiens* seed.

9. The method of claim 8, wherein the method further comprises:
   (a) crossing a plant grown from said F1 hybrid *Impatiens* seed with itself or a different *Impatiens* plant to produce a seed of a progeny plant of a subsequent generation;
   (b) growing a progeny plant of a subsequent generation from said seed of a progeny plant of a subsequent generation.

10. The method of claim 9, further comprising
    (c) crossing the progeny plant of a subsequent generation with itself or a second plant to produce a progeny plant of a further subsequent generation.

11. An F1 hybrid *Impatiens* seed comprising said locus produced by the method of claim 8.

12. An *Impatiens walleriana* plant having resistance to downy mildew relative to a wild type plant, wherein said *Impatiens walleriana* plant comprises the genetic source for downy mildew resistance that is found in *Impatiens* sp. 7511, wherein a representative deposit of seed comprising said genetic source has been made under ATCC Accession No. PTA-123803.

13. The plant of claim 12, wherein said plant comprises SEQ ID NO:4 or SEQ ID NO:5.

14. The plant of claim 12, wherein the plant is inbred.

15. The plant of claim 12, wherein the plant is hybrid.

16. A plant part of the plant of claim 12, wherein the plant part comprises at least one cell of said plant.

17. A seed that produces the plant of claim 12.

18. A method of producing a downy mildew resistant *Impatiens* seed, the method comprising crossing the plant of claim 12 with itself or a second *Impatiens* plant.

* * * * *